(12) United States Patent
Jadhav et al.

(10) Patent No.: US 9,796,750 B2
(45) Date of Patent: Oct. 24, 2017

(54) PROCESS FOR THE PURIFICATION OF FLUTICASONE PROPIONATE USING A KETONE SOLVENT AND WATER AS ANTI-SOLVENT

(71) Applicant: Mylan Laboratories Ltd., Hyderabad (IN)

(72) Inventors: Sakharam Jadhav, Hyderabad (IN); Chandersingh Bohara, Hyderabad (IN); Ghanshyam Wagh, Hyderabad (IN); Vinayak Govind Gore, Hyderabad (IN); Maheshkumar Gadakar, Hyderabad (IN)

(73) Assignee: Mylan Laboratories Ltd., Hyderabad (IN)

( * ) Notice: Subject to any disclaimer, the term of this patent is extended or adjusted under 35 U.S.C. 154(b) by 0 days.

(21) Appl. No.: 15/116,859

(22) PCT Filed: Feb. 5, 2015

(86) PCT No.: PCT/IB2015/050871
§ 371 (c)(1),
(2) Date: Aug. 5, 2016

(87) PCT Pub. No.: WO2015/118474
PCT Pub. Date: Aug. 13, 2015

(65) Prior Publication Data
US 2017/0174719 A1    Jun. 22, 2017

(30) Foreign Application Priority Data
Feb. 7, 2014  (IN) .............................. 572/CHE/2014

(51) Int. Cl.
*C07J 31/00*    (2006.01)

(52) U.S. Cl.
CPC ................................... *C07J 31/006* (2013.01)

(58) Field of Classification Search
CPC ....................................................... C07J 31/006
See application file for complete search history.

(56) References Cited

U.S. PATENT DOCUMENTS

| | | | |
|---|---|---|---|
| 4,335,121 A | 6/1982 | Phillipps et al. | |
| 2004/0220157 A1 | 11/2004 | Biggadike et al. | |
| 2014/0141247 A1* | 5/2014 | Ticehurst | C07J 31/006 428/402 |

FOREIGN PATENT DOCUMENTS

| WO | WO 2012/029077 A2 | 3/2012 |
|---|---|---|
| WO | WO 2013/009591 A1 | 1/2013 |

OTHER PUBLICATIONS

Hursthouse et al, Organic Process Research & Development, Why Do Organic Compounds Crystallise Well or Badly or Ever so Slowly? Why Is Crystallisation Nevertheless Such a Good Purification Technique?, 2009, 73, pp. 1231-1240.*
Zauner, Scale-up of Precipitation Processes, 1994, Ph.D. Thesis, Ramsay Memorial Laboratory of Chemical Engineering, University College London.*
Murnane, D., et al., "Crystallization and Crystallinity of Fluticasone Propionate," *Crystal Growth & Design*, Aug. 1, 2008, pp. 2753-2764, vol. 8(8), American Chemical Society.

* cited by examiner

*Primary Examiner* — Paul A Zucker

(57) ABSTRACT

The present disclosure relates to an improved process for the preparation of fluticasone propionate.

4 Claims, No Drawings

PROCESS FOR THE PURIFICATION OF FLUTICASONE PROPIONATE USING A KETONE SOLVENT AND WATER AS ANTI-SOLVENT

CROSS-REFERENCE TO RELATED APPLICATIONS

This application is a national phase entry of PCT International Application No. PCT/IB2015/050871, filed Feb. 5, 2015, which claims priority to Indian Provisional Patent Application No. 572/CHE/2014, filed Feb. 7, 2014, the contents of each of which are hereby incorporated herein in their entirety by reference.

BACKGROUND OF THE INVENTION

Field of the Disclosure

The present disclosure relates to an improved process for the preparation of fluticasone propionate.

Description of the Related Art

Fluticasone propionate is a corticosteroid of the androstane family which has potent anti-inflammatory activities and is widely accepted as a useful therapy for the treatment of inflammatory and allergic conditions such as asthma and chronic obstructive pulmonary disease (COPD).

Fluticasone propionate is chemically named as 6α, 9α-difluoro-17α-(((fluoromethyl) sulfanyl) carbonyl)-11β-hydroxy-16α-methyl-3-oxoandrosta-1,4-dien-17α-yl propionate and is represented by the following chemical structure:

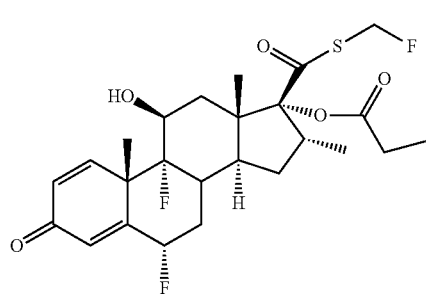

Formula I

U.S. Pat. No. 4,335,121 discloses a process for the preparation of fluticasone propionate, wherein 6α,9α-difluoro-11β-hydroxy-16α-methyl-3-oxo-17α-(propionyloxy) androsta-1,4-diene-17β-carboxylic acid of formula IV is treated with dimethylthiocarbamoyl chloride to yield 17β-(N,N(dimethylcarbamoyl)thio)carbonyl-6α,9α-difluoro-11β-hydroxy-16α-methyl-17α-propiony-loxy-3-oxoandrosta-1,4-diene of formula III. This is hydrolyzed by refluxing in diethyl amine to obtain the thioic acid of formula II. The compound of formula II is then reacted with bromochloromethane in the presence of sodium bicarbonate to give a chloromethylester of formula IIa. The compound of formula IIa is converted to an iodomethylester by halogen exchange, and subsequently treated with silver fluoride to yield the fluticasone propionate of formula I. The reaction steps are illustrated by the following scheme:

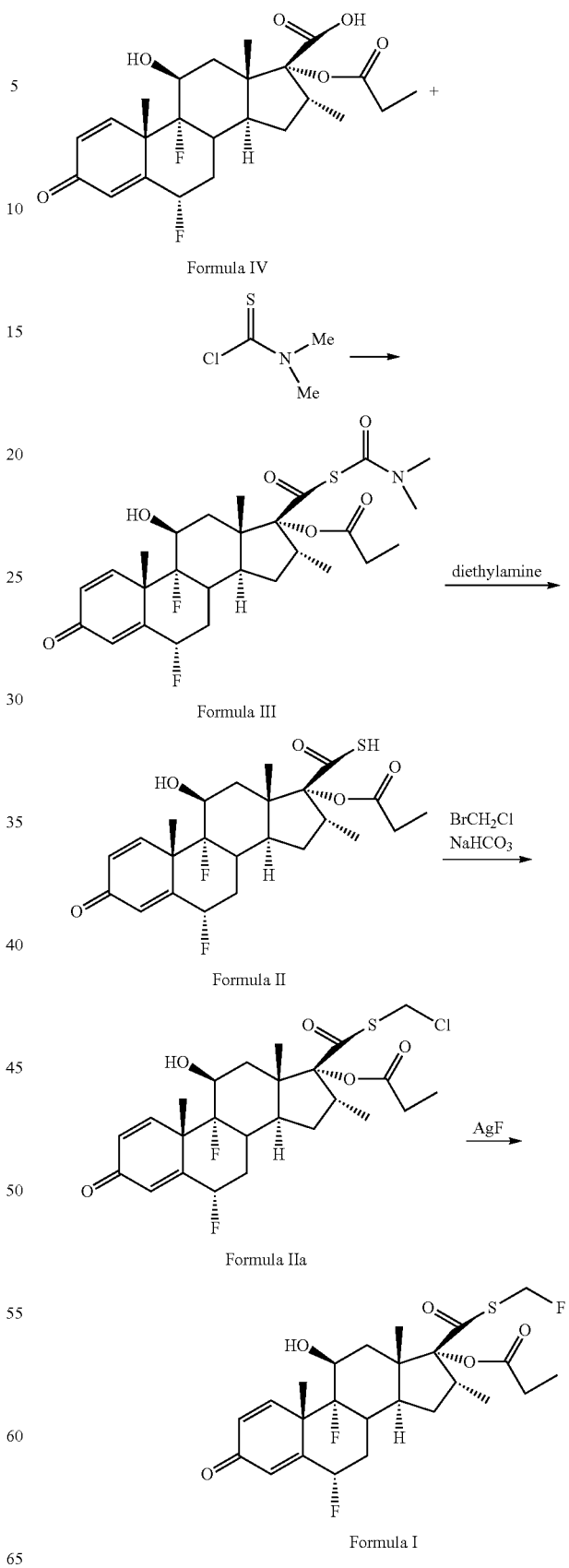

SUMMARY OF THE DISCLOSURE

One aspect of the present disclosure is to provide an improved process for the preparation of fluticasone propionate.

In one embodiment, the present disclosure provides an improved process for the preparation of fluticasone propionate comprising the steps of:
a) dissolving fluticasone propionate in a ketone solvent to produce a mixture,
b) heating the mixture slowly for 1-2 hours to get a clear solution,
c) adding water to the step (b) solution at 50-60° C.,
d) cooling to −5° C. to 10° C., and
e) isolating fluticasone propionate.

In another embodiment, the present disclosure provides an improved process for the preparation of fluticasone propionate having a particle size less than 400 microns.

In other embodiments of the present disclosure, the obtained fluticasone propionate particles are used for formulating pharmaceutical compositions.

DETAILED DESCRIPTION OF THE DISCLOSURE

It is to be understood that the description of the present invention has been simplified to illustrate elements that are relevant for a clear understanding of the invention, while eliminating, for purposes of clarity, other elements that may be well known.

More specifically, the present disclosure relates to an improved process for the preparation of fluticasone propionate.

One embodiment of the present disclosure is to provide an improved process for the preparation of fluticasone propionate comprising the steps of:
a) dissolving fluticasone propionate in a ketone solvent to produce a mixture,
b) heating the mixture slowly for 1-2 hours to get a clear solution,
c) adding water to the step (b) solution at 50-60° C.,
d) cooling to −5° C. to 10° C., and
e) isolating fluticasone propionate.

According to the present disclosure, fluticasone propionate is dissolved in a ketone solvent at 25-30° C. The temperature of the solution is raised to 50-60° C. and water is added to the above solution slowly at 50-60° C. over the period of 1-2 hours to get the precipitation. The precipitated mixture is cooled to −5° C. to 10° C. and stirred for 1 hour. The obtained solid is filtered and washed with a ketone solvent/water mixture. The compound is dried under the vacuum to get crystalline fluticasone propionate in desired particle size.

Within the context of the present disclosure, the ketone solvent employed above may include, but is not limited to, acetone, butanone, methyl isobutyl ketone, methyl ethyl ketone, methyl tertiary butyl ketone, and mixtures thereof. Again, one of skill in the art will recognize numerous additional ketone solvents that may be employed as a solvent. In certain embodiments, it has been found that acetone is a particularly useful solvent.

According to the present embodiment, the obtained fluticasone propionate in the present disclosure may be amorphous or crystalline in nature and it may be in anhydrous or hydrated crystalline form.

According to the present disclosure, fluticasone propionate may be prepared as per the prior art process disclosed in U.S. Pat. No. 4,335,121. The initial particle size of fluticasone propionate employed for this disclosure is in the range of 50-75 microns.

According to the present embodiment, the obtained fluticasone propionate has a particle size d90 of less than 400 microns, d50 of less than 200 microns and d10 of less than 100 microns. In a particular embodiment, the size of the particle is further micronized/sieved to get the desired particle size of d90 in the range of 307.3 microns, d50 in the range of 105.3 microns and d10 in the range of 32.7 microns.

In another embodiment of the present disclosure, the obtained fluticasone propionate particles are used for formulating the pharmaceutical composition.

The following examples are provided for illustrative purposes only and are not intended to limit the scope of the disclosure in any way.

EXPERIMENTAL SECTION

Example-1

Preparation of Crystalline Fluticasone Propionate

Fluticasone propionate (50 gm, particle size d (90)=50-75 micron) was dissolved in an acetone (1225 ml) solvent at 25-30° C. The mixture was heated to 35-45° C. and maintained for 30 minutes to get a clear solution. The clear solution was filtered through the (0.45 micron) filter paper. The temperature was raised to 50-60° C. To the above clear solution, water (562.5 ml) was added at 50-60° C. over a period of 60 to 105 minutes with controlled rate, and the reaction mass was stirred for 15-30 min. The reaction mass was cooled to an ambient temperature of 24-30° C. and stirred for 14-15 hours. The reaction mass was cooled to −5° C.-10° C. gradually and further stirred for 1 hour to get solid. The obtained solid is filtered and washed with an acetone/water mixture (21.75 ml; 15 ml of acetone mixed with 6.75 ml of water). The compound is dried under the vacuum and sieved to get crystalline fluticasone propionate.
Wt: 45 gms
Particle size:
d (10)=32.7 micron.
d (50)=105.3 micron.
d (90)=307.3 micron.

The invention claimed is:
1. An improved process for the preparation of fluticasone propionate comprising the steps of:
a) dissolving fluticasone propionate in a ketone solvent to produce a mixture,
b) heating the mixture for 1-2 hours to get a clear solution,
c) adding water to the step (b) solution, wherein the step (b) solution is at 50-60° C.,
d) cooling to −5° C. to 10° C., and
e) isolating fluticasone propionate;
wherein the ketone solvent is selected from the group consisting of acetone, butanone, methyl isobutyl ketone, methyl ethyl ketone, methyl tertiary butyl ketone, and mixtures thereof.

2. The process according to claim 1, wherein the obtained fluticasone propionate has a particle size d90 of less than 400 microns, d50 of less than 200 microns and d10 of less than 100 microns.

3. The process according to claim 2, further comprising the step of:
f) micronizing or sieving the isolated fluticasone propionate.

4. The process according to claim 3, wherein the obtained fluticasone propionate has a d90 particle size of 307.3 microns, a d50 particle size of 105.3 microns and a d10 particle size of 32.7 microns.

\* \* \* \* \*